US005522900A

United States Patent [19]
Hollister

[11] Patent Number: 5,522,900
[45] Date of Patent: Jun. 4, 1996

[54] PROSTHETIC JOINT AND METHOD OF MANUFACTURE

[75] Inventor: Anne Hollister, Downey, Calif.

[73] Assignee: Avanta Orthopaedics, San Diego, Calif.

[21] Appl. No.: 169,297

[22] Filed: Dec. 17, 1993

[51] Int. Cl.$^6$ .................................................. A61F 2/30
[52] U.S. Cl. ............................ 623/18; 623/901; 128/898
[58] Field of Search .................................. 623/18, 20, 21, 623/66, 901; 128/898

[56] References Cited

U.S. PATENT DOCUMENTS

| | | |
|---|---|---|
| 4,021,864 | 5/1977 | Waugh . |
| 4,178,640 | 12/1979 | Buechler . |
| 4,229,841 | 10/1980 | Youm et al. . |
| 4,242,759 | 1/1981 | White ........................................ 623/21 |
| 4,349,922 | 9/1982 | Agee . |
| 4,944,758 | 7/1990 | Bekki et al. . |
| 4,959,071 | 9/1990 | Brown et al. . |
| 5,037,440 | 8/1991 | Koenig ..................................... 623/21 |
| 5,133,758 | 7/1992 | Hollister . |

FOREIGN PATENT DOCUMENTS

| | | |
|---|---|---|
| 0350371 | 1/1990 | European Pat. Off. . |
| 2519865 | 11/1976 | Germany . |
| 2045085 | 10/1980 | United Kingdom . |

OTHER PUBLICATIONS

Benaim et al., "Minimization of the Gliding Index: . . . " Journal of Biomechanics; vol. 20, No. 9, 1987.

Pennock et al., "An Anatomy Based Coordinate System for the Description of Kinematic Displacements in the Human Knee," vol. 23, No. 12, 1990.

Hollister et al., "The Axes of Rotation of the Knee," Clinical Orthopaedics and Related Research; No. 290, pp. 259–268, May 1993.

Brand et al., Clinical Mechanics of the Hand, pp. 35–59, 1985, Mosby Year Book.

Thompson et al., A Hand Biomechanics Workstation, pp. 335–343, Aug. 1988, Computer Graphics, vol. 22, No. 4.

Ateshian et al., Determination of Thumb Carpometacarpal Joint Contact in Lateral Pinch, Aug. 30–Sep. 4, 1990, First World Congress of Biomechanics.

Giurintano et al., Force Analysis of the Thumb for a Five-Link System, ASME 1991, AMD-vol. 120, 1991 Biomechanics Symposium.

Hollister et al., The Axes of Rotation of the Thumb Carpometacarpal Joint, Oct. 12, 1990–Dec. 3, 1991, Journal of Orthopaedic Research.

Hollister, et al., Off Set Hinges: A General Theory for Synovial Joint Kinematics; Undated, Department of Rehabilitation Research, Carville, LA 70721.

Primary Examiner—David Isabella
Assistant Examiner—Laura Fossum
Attorney, Agent, or Firm—Nydegger & Associates

[57] ABSTRACT

A method for modeling a prosthetic joint, and the joint manufactured therefrom, involves anatomically locating the two non-perpendicular and non-intersecting axes of rotation for the joint. The surface of revolution about these two axes, which is a torus, is then used to mathematically model the bearing surfaces of the prosthetic joint.

6 Claims, 2 Drawing Sheets

PROSTHETIC JOINT AND METHOD OF MANUFACTURE

FIELD OF THE INVENTION

The present invention pertains generally to prosthetic replacement joints. More particularly, the present invention pertains to two-member joints having members with respective corresponding surfaces that mate and move relative to each other for simultaneous rotation of the members about two separate axes of rotation. The present invention is particularly, but not exclusively, useful as a prosthetic joint for duplicating anatomical movement of a joint in the human skeleton.

BACKGROUND OF THE INVENTION

Nature has created many of the skeletal joints of the human anatomy such that the movement of one bone relative to the other bone, or bones, at the joint is best described as a rotational motion within a definable envelope. Specifically, the normal movement of a bone at a joint is a rotation of the bone about two different axes which are non-perpendicular and non-intersecting. Several mechanical advantages result from this fact. First, the kinematics of anatomical joints allows for more than just simple rotation in a plane. Specifically, because the two axes of rotation are non-perpendicular and non-intersecting, rotation of the bone about these two axes manifests rotations in all three anatomical planes (sagittal, transverse and coronal). Equally important, because only two axes of rotation are involved, anatomical joints require fewer muscles to achieve this rotation of a bone about the joint than would be required for a structure which uses three axes of rotation to achieve the same movement. Thus, anatomical joints are very mechanically efficient. The result of all this is what people perceive as normal skeletal movement.

Many prosthetic replacements for diseased or damaged joints have been developed and used over the years. Clearly, the intention in developing these joints has been to effectively duplicate the natural kinematics of the particular anatomical joint that is to be replaced. To do this, however, there has been no attempt to duplicate or mimic the natural boney structure of the joint. Instead, prosthetic joint designs have typically been driven by conventional considerations of joint movement relative to the anatomical reference planes. This has caused many to overlook the fact that normal bone movement about a joint can involve simultaneous interrelated movements in all of the reference planes. As a consequence of the conventional approaches used to design prosthetic replacement joints, the joints have been designed with either a single axis of rotation or with orthogonal axes of rotation. For example, U.S. Pat. No. 4,944,758, which issued to Bekki et al. for an invention entitled "Artificial Finger Joint", discloses a single axis joint which guides one member of the joint as it bends relative to the other joint member in a prescribed direction. As another example of conventionally designed prosthetic replacement joints, U.S. Pat. No. 4,229,841, which issued to Youm et al. for an invention entitled "Wrist Prosthesis", discloses a joint which provides for relative movement of the components about two substantially perpendicular axes. As an example of a three axes prosthesis, U.S. Pat. No. 4,349,922, which issued to Agee for and invention entitled "Joint Prosthesis with Improved Articulation Means", discloses a combination of linking pins which allows for members of the joint to pivot about three different axes. Unlike the above cited references which include interconnected members, U.S. Pat. No. 4,959,071, which issued to Brown et al. for an invention entitled "Partially Stabilized Knee Prosthesis", discloses a prosthetic joint which includes members that are not interconnected, but which rotatably slide relative to each other. Still, despite this distinction, the prosthetic joint disclosed by Brown et al. is restricted to rotation about a single axis.

None of the above cited references either teach or suggest designing a prosthetic replacement joint by first analyzing the kinematics of the joint itself. If this were done, the naturally occurring two non-perpendicular and non-intersecting axes of rotation, which are characteristic of a normal joint, would become evident. With this in mind, the present invention has recognized that the abutting surfaces of normal bones at a joint are surfaces of revolution. Specifically, each of the abutting surfaces of the bones at a joint is a surface of revolution about the joint's two non-perpendicular and non-intersecting anatomical axes of rotation. Further, the present invention recognizes that this surface of revolution is a torus, and specifically a skewed torus, which has parameters that can be geometrically varied to recreate the particular bone joint surface of interest. Using these observations, the present invention recognizes that the boney structures of an anatomical joint can be reproduced for a prosthesis and employed to restore normal joint kinematics.

In light of the above it is an object of the present invention to provide a method for modeling a prosthetic joint which produces a prosthetic replacement joint which will restore normal joint kinematics. Another object of the present invention is to provide a method for modeling a prosthetic joint which produces a prosthetic replacement joint that maintains the mechanical advantage of the muscles which cross the joint. Still another object of the present invention is to provide a method for modeling a prosthetic joint which produces a prosthetic replacement joint which recreates the normal joint's axes of rotation. Yet another object of the present invention is to provide a method which can be employed for modeling different types of prosthetic replacement joints. Another object of the present invention is to provide a method for modeling prosthetic replacement joint which is relatively easy to accomplish and comparatively cost effective.

SUMMARY OF THE INVENTION

The prosthetic joint of the present invention, and its method of manufacture, pertains to a two-member joint which relies on the identification and location of two separate axes of rotation that will serve as the basic references from which anatomical movement of the joint is duplicated. Both of these axes, and their location relative to each other, are anatomically identifiable and are unique for the particular joint to be duplicated. One of the axes, the first axis, is anatomically referenced relative to one member of the joint. The other axis, the second axis, is also anatomically correct and is located with a predetermined relationship to the first axis. Typically, these axes of rotation are not perpendicular and do not intersect. Stated differently, the predetermined relationship between the first and second axis is characterized by a first off-set angle ($\alpha$), a second offset angle ($\beta$), and the projected distance between the two axes.

As indicated above, the prosthetic joint of the present invention includes two members. A first member of the joint has a first surface which is generated mathematically as a surface of revolution about both the first axis and the second axis. A second member of the joint has a second surface which mates with the first surface of the first member. Through this relationship, the second member is able to rotate relative to the first member about both the first axis and the second axis.

The actual topography and shape of the first and second surfaces for the respective members of the joint are determined by the location of these interfacing surfaces relative to the first and second axes of rotation. For purposes of the present invention, the location of the interfacing first and second surfaces is determined anatomically. Depending on the particular joint to be duplicated, it can be either proximal to both axes, intermediate to the axes, or distal to both axes.

The range of motion of the joint is determined both by the shapes of the interfacing surfaces, and by the dimensions of these surfaces. More specifically, the range of motion is determined mathematically by the number of degrees of rotation desired about each axes of rotation. Further, insofar as dimensions are concerned, in order for members of the joint to remain in contact and effectively duplicate a normal anatomical range of motion, the surface of the first member could have an area which is larger than the surface area of the second member. The second member is then able to effectively rotate about both axes of rotation as its second surface moves over the first surface of the first member.

As intended for the present invention, for a joint replacement, one member of the prosthetic joint is attached and anchored to the proximal bone of the original joint. The other member of the joint is then attached and anchored to the distal bone, or bones, of the original joint. The members of the prosthetic joint are then juxtaposed at their respective rotational surfaces to kinematically duplicate the joint which needed to be replaced.

The novel features of this invention, as well as the invention itself, both as to its structure and its operation will be best understood from the accompanying drawings, taken in conjunction with the accompanying description, in which similar reference characters refer to similar parts, and in which:

Figure 1:
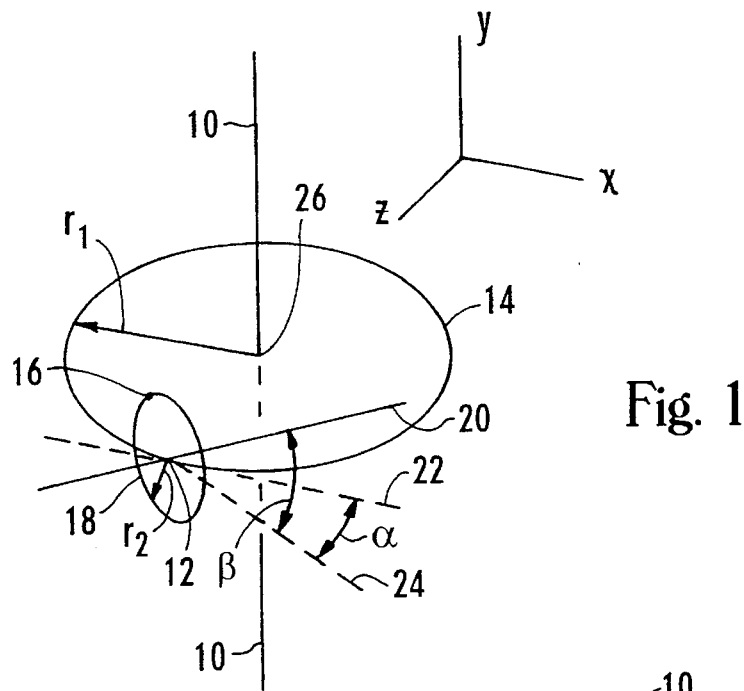
FIG. 1 is an isometric depiction of the geometric considerations for generation of a torus.

When initially considering the geometric relationships of FIG. 1, it may be less confusing to not attempt to relate the x-y-z axis systems shown to the conventional anatomical reference planes. This relationship is best made after the geometries involved are established.

DESCRIPTION OF THE PREFERRED EMBODIMENTS

To begin, consider FIG. 1 and the geometric relationships depicted which are helpful for a mathematical understanding of the present invention.

In FIG. 1, a first axis 10 is shown arbitrarily directed in the y direction of the x-y-z coordinate system. Consider now a point 12 in the x-y-z system which does not lie on the axis 10. It is clear that, if the point 12 is rotated about the axis 10 at a fixed distance $r_1$ from the axis 10 and in a plane which is perpendicular to the axis 10, the point 12 will follow a circular path 14. For the geometry shown in FIG. 1, the circular path 14 is shown to be in the x-z plane and $r_1$ is the radius of the resultant circle.

Next, consider the rotation of a point 16 around the point 12. Such a rotation will result in a circular path 18, if the point 16 stays at a fixed distance $r_2$ from the point 12 and remains in a plane which is perpendicular to an axis 20 passing through the point 12. For this rotation, $r_2$ is the radius of the resultant circle. The exact orientation of circular path 18 relative to circular path 14 is also important for a complete understanding of the geometry involved with the present invention. To establish this orientation, axis 20 can be described by the off-set angles $\alpha$ and $\beta$. Specifically, the angle $\alpha$ is defined as the angle between a line 22 which lies in the x-z plane tangent to path 14 at point 12 and the projection 24 of axis 20 in the x-z plane. The angle $\beta$ is then defined as the angle between the axis 20 and its projection 24 in the x-z plane.

Figure 2:
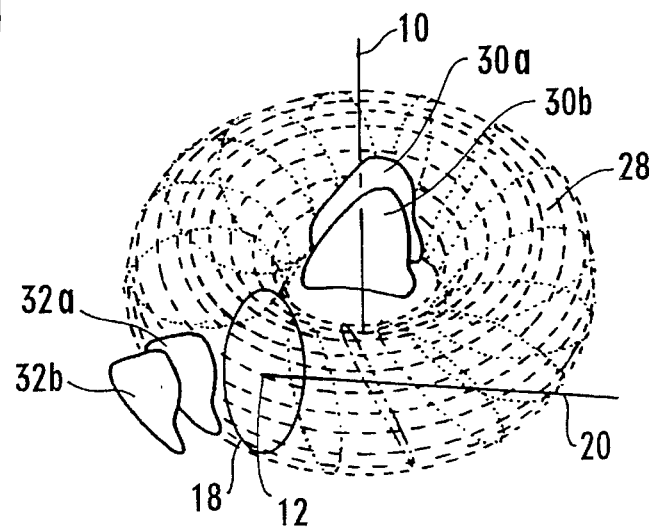
FIG. 2 is an isometric view of a torus with surface portions thereof selected for use as abutting surfaces of the prosthetic replacement joint of the present invention.

By definition, a torus is a solid which is generated by rotating a circle about an external point in its plane. In FIG. 1, the circle is established by the circular path 18 and the external point is the point 26 where axis 10 intersects the x-z plane. Thus, if circular path 18 is rotated around axis 10, along circular path 14, the torus 28 of FIG. 2 is generated. Recognize at this point that the variable geometric parameters involved in generating torus 28 are: i) radius $r_1$, ii) radius $r_2$, iii) angle $\alpha$, and iv) angle $\beta$. For the most trivial case where both of the angles $\alpha$ and $\beta$ are zero degrees, and depending on the values given to $r_1$ and $r_2$, the torus 28 will be doughnut shaped and be either a very thin or a very fat doughnut. It happens, however, that the range of values for both $\alpha$ and $\beta$ are between zero and one hundred and eighty degrees (0°–180°). Accordingly, with values give to the angles $\alpha$ and $\beta$, as is normally the case, the torus 28 can be skewed.

Recall the observation previously made that many anatomical joints cause a member to rotate about two axes that are non-perpendicular and non-intersecting. This is the same as the case for the skewed torus 28. The present invention incorporates this notion.

Referring to FIG. 2, a portion of the surface of skewed torus 28 is shown and designated 30a. Along with the surface 30a, a surface 30b is also shown. For purposes of illustration only, the surface 30b is shown to be slightly distanced from the surface 30a. Geometrically, the surfaces 30a and 30b conform, or mate, with each other in the position shown. In effect, surface 30a and 30b have a male-female relationship with each other. Similarly, other portions of the skewed torus 28 are shown as the surfaces 32a and 32b. The surfaces 30a and 30b, however, differ from the surfaces 32a and 32b in their relationships with the first axis of rotation 10 and their respective second axis of rotation 20 (Note: axis 20 is not shown in its position for the surfaces 30a and 30b).

As indicated above, the surfaces of bones which abut each other at a joint are typically surfaces of revolution similar to the surface of skewed torus 28. Accordingly, the surfaces 30a–30b and the surfaces 32a–32b of skewed torus 28, if properly dimensioned, will duplicate or mimic the bone surfaces of anatomical joints.

Figure 3:
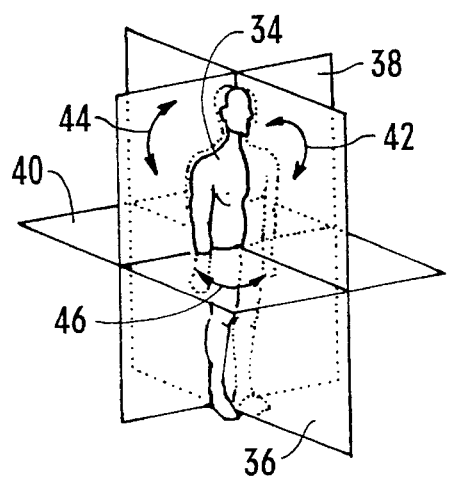
FIG. 3 is an isometric view of a human being shown in relationship to the three anatomical reference planes.

In order to relate the geometry of skewed torus 28 to the human body, consider the generic man 34 shown in FIG. 3. By convention, movements of generic man 34 are referenced to three anatomical planes. These are: the sagittal plane 36, the coronal plane 38, and the transverse plane 40. Depending on the positioning of the reference planes 36, 38 and 40, any movement of generic man 34 can be described as a rotation in one or more of these planes. Specifically, rotations in the sagittal plane 36 are shown by arrow 42 to indicate movements in flexion and extension, rotations in the coronal plane 38 are shown by arrow 44 to indicate movements in abduction and adduction, and rotations in the transverse plane 40 are shown by arrow 46 to indicate external and internal movements.

Now compare FIG. 3 with FIGS. 1 and 2, and, more specifically, consider the movement of point 16 along circular path 18. Also, imagine the x-y-z coordinate system with the y axis aligned on axis 10, and the z axis intersecting point 12. If angles $\alpha$ and $\beta$ have values which are greater than zero, the projection of circular path 18 onto the x-y plane (compare with sagittal plane 36) will indicate some rotation in either flexion or extension. Similarly, the projection of circular path 18 onto the y-z plane (compare with coronal plane 38) will indicate some rotation in either abduction or adduction. Likewise, by projecting circular path 18 onto the x-z plane (compare with transverse plane 40), an internal or external rotation is indicated. Therefore, in accord with the anatomical reference planes 36, 38 and 40 of generic man 34, any movement along the surface of skewed torus 28 is manifested as movements of flexion-extension, abduction-adduction, and external-internal. The consequence of this is that prosthetic joints which have abutting surfaces similar to the surfaces 30a,b or 32a,b can be properly dimensioned to duplicate or mimic the replaced anatomical joint.

Figure 4:
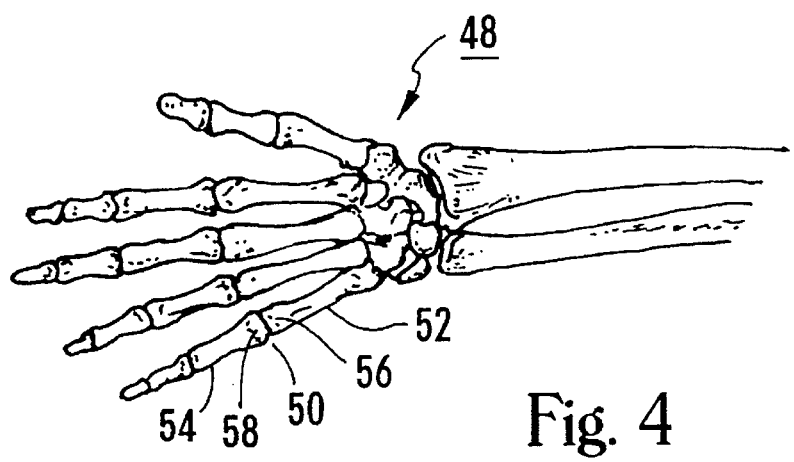
FIG. 4 is a plan view of the skeleton of a hand.

Referring now to FIG. 4 the skeleton of a hand of generic man 34 is shown and generally designated 48. The hand 48 is shown here only for exemplary purposes and it is to be understood that other anatomical structures could as easily be discussed in the context of the present invention. Nevertheless, hand 48 is shown with a finger joint 50 which connects the bone member 52 with the bone member 54. More specifically, a surface 56 of bone member 52 abuts a surface 58 of the bone member 54. Consequently, the bone surfaces 56 and 58 move relative to each other as the bone member 52 is rotated about the finger joint 50. As indicated above, surfaces 56 and 58 will very closely resemble a portion or area on the surface of a skewed torus 28. In accordance with the present invention, if the finger joint 50 needs to be replaced, a prosthetic joint having surfaces 30a–30b or 32a–32b needs to be manufactured.

Recall, many anatomical joints, like finger joint 50, are characterized by two axes of rotation which are non-perpendicular and non-intersecting. Thus, using the geometrical parameters set out in FIG. 1, the joint 50 has a first axis 10 and a second axis 20. It happens that both an axis 10 and an axis 20 can be anatomically identified and located for the finger joint 50. This identification can be accomplished in a manner well known in the art, and will apply for other joints in the skeleton of generic man 34 as well as for the joint 50. Note, having identified axis 10 and axis 20 and their relationship to each other, the off-set angles $\alpha$ and $\beta$ are determined. Also, the intersection between bone surfaces 56 and 58 can be anatomically located for the joint 50 relative to the axes 10 and 20. With the location of the intersection between bone surfaces 56 and 58, the radii $r_1$ and $r_2$ of the skewed torus are established. Consequently, by making simple anatomical measurements of the joint 50, the parameters $\alpha$, $\beta$, $r_1$, and $r_2$ of skewed torus 28 are determined.

Figures 5A, 5B:
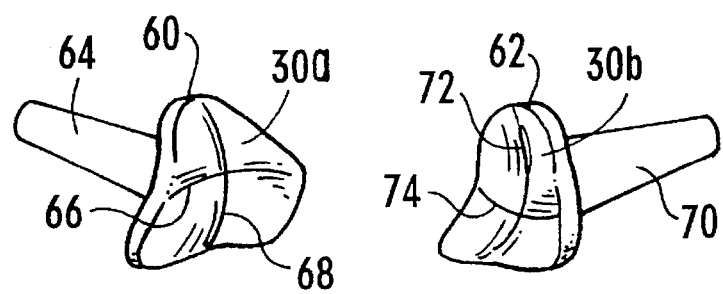
FIGS. 5A and 5B are different angle perspective views of mating surfaces taken from the torus shown in FIG. 2 for use in a prosthetic joint wherein the joint surfaces are between the two axes of rotation which define the torus.

Using anatomical measurements for the parameters $\alpha$, $\beta$, $r_1$, and $r_2$, the surfaces 30a–b or 32a–b can be generated mathematically. This information can then be used to manufacture mating prosthetic members 60 and 62 which are shown respectively in FIGS. 5A and 5B. Referring first to FIG. 5A the prosthetic member 60 is shown with a bearing surface 30a that has a stem 64 attached thereto. The bearing surface 30a is the same as surface 30a of skewed torus 28 and is characterized by a concavity (indicated by the line 66), and a convexity (indicated by the line 68). Similarly, prosthetic member 62 has an attached stem 70. Also, member 62 has a bearing surface 30b which is the same as the surface 30b of skewed torus 28. As can be appreciated by cross referencing FIG. 5A with 5B, the bearing surface 30b of member 62 has a concavity (indicated by line 72) which conforms to the convexity of bearing surface 30a on member 60. Also, bearing surface 30b of member 62 has a convexity (indicated by line 74) which conforms to the concavity of bearing surface 30a on member 60. Thus, prosthetic members 60 and 62 have mating surfaces.

Figures 6A, 6B:
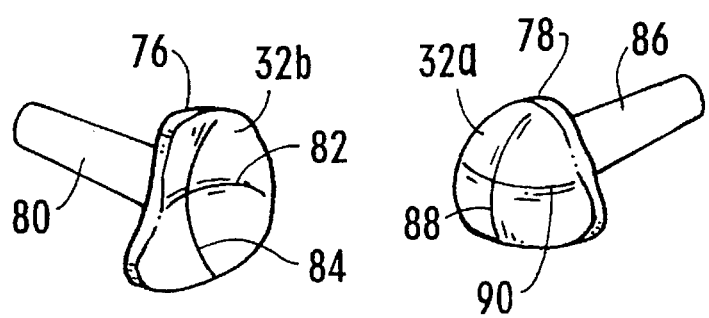
FIGS. 6A and 6B are different angle perspective views of mating surfaces from the torus shown in FIG. 2 for use in a prosthetic joint wherein the joint surfaces are proximal to or distal from the two axes of rotation which define the torus.

As discussed here, the prosthetic members 60 and 62 have bearing surfaces 30a–b which are needed when the abutting surfaces of the anatomical joint being replaced are between the axes 10 and 20. On the other hand, if the abutting surfaces of the anatomical joint which is being replaced are both either proximally or distally located in their relationship to the axes 10 and 20, then a mating pair of prosthetic members having bearing surfaces which are the same as surfaces 32a–b will be required. FIGS. 6A and 6B show such a pair of prosthetic members.

FIGS. 6A and 6B respectively show a prosthetic member 76 having a bearing surface 32b and a prosthetic member 78 having a bearing surface 32a. In FIG. 6A it will be seen that the member 76 includes an attached stem 80 and that the bearing surface 32b is concave, as indicated by the lines 82 and 84. FIG. 6B, shows that prosthetic member 78 includes an attached stem 86 and that the bearing surface 32a is convex, as indicated by the lines 88 and 90. Because the bearing surfaces 32a and 32b conform to each other, they will mate with each other when juxtaposed.

In an operation for the replacement of the finger joint 50 shown in FIG. 4, the rotational axes 10 and 20 are located on the joint 50 to determine the anatomical parameters $\alpha$, $\beta$, $r_1$ and $r_2$. A pair of prosthetic members 60,62 (or 76,68), which have manufactured with dimensions that comply with the anatomical, parameters $\alpha$, $\beta$, $r_1$ and $r_2$ are selected. After properly preparing the bones 52 and 54, in a manner well known to orthopedic surgeons, the prosthetic members 60,62 are attached to the bones 52 and 54 to correctly mimic the anatomical structure of the joint being replaced. The original muscles and ligaments associated with joint 50 are then reconnected, if possible, and the prosthetic joint comprising the prosthetic members 60,62 is set. Bones 52 and 54 will then be enabled to move relative to each other in a manner which will duplicate and mimic their natural rotation around two non-perpendicular and non-intersecting axes of rotation.

While the particular method for modeling a prosthetic joint, and the resultant joint, as herein shown and disclosed in detail is fully capable of obtaining the objects and providing the advantages herein before stated, it is to be understood that it is merely illustrative of the presently preferred embodiments of the invention and that no limitations are intended to the details of the construction or design herein shown other than as defined in the appended claims.

I claim:

1. A method for modeling a prosthetic joint, for replacement of an anatomical joint having first and second bones wherein the second bone moves relative to the first bone by simultaneous pivoting about two non-intersecting and non-orthogonal axes of rotation, the method comprising the steps of:

locating a first said axis of rotation of the second bone relative to the first bone;

locating a second said axis of rotation of the second bone relative to the first bone;

locating a curved mating surface on said second bone, said mating surface being the surface at which the second bone mates with the first bone;

determining a first radius from said second axis to a circular arc in the curved mating surface, the center of said circular arc being a point on said second axis, said circular arc lying in a first reference plane which is perpendicular to said second axis at said center of said circular arc;

establishing a second reference plane perpendicular to said first axis and passing through said center of said circular arc;

defining an angle and measuring an angular variation of said angle between said first axis and said second axis at the intersection of said second axis with said second reference plane;

determining a second radius from said first axis to said second axis, as measured in said second reference plane;

mathematically generating a reference circle by completing said circular arc in said first reference plane;

mathematically generating a reference toroid defining a surface by rotating said reference circle about said first axis at said second radius;

selecting a portion of said surface of said reference toroid to substantially duplicate the mating surface;

forming a first joint surface on a first member of said prosthetic joint, said first joint surface duplicating the topography of said selected surface portion of said toroid; and forming a second joint surface on a second member of said prosthetic joint, said second joint surface duplicating the topography of said selected surface portion of said toroid.

2. A method as recited in claim 1 wherein said angular variation consists of:

a first angle between a projection of said second axis in said second reference plane and a line tangent to a circle defined by rotating said second axis about said first axis at said second radius; and a second angle between said second axis and said second reference plane.

3. A method as recited in claim 1 wherein said second axis is located intermediate said first axis and said selected surface portion of said toroid.

4. A method as recited in claim 1 wherein said selected surface portion of said toroid is located intermediate said first axis and said second axis.

5. A method as recited in claim 1 wherein said first joint surface has a surface area and said second joint surface has a surface area and wherein said surface area of said first joint surface is greater than said surface area of said second joint surface.

6. A method as recited in claim 5 further comprising the step of dimensioning said first joint surface to cause said prosthetic joint to have a range of motion which effectively duplicates a range of motion of said anatomical joint.

* * * * *